(12) United States Patent
Tomasetti et al.

(10) Patent No.: US 6,236,712 B1
(45) Date of Patent: May 22, 2001

(54) MINIATURE C-ARM APPARATUS WITH MULTIPLE X-RAY INDICATORS

(75) Inventors: Perry J. Tomasetti, Elmwood Park; William E. Higgins, Palos Heights, both of IL (US)

(73) Assignee: FluoroScan Imaging Systems, Inc., Northbrook, IL (US)

( * ) Notice: Subject to any disclaimer, the term of this patent is extended or adjusted under 35 U.S.C. 154(b) by 0 days.

(21) Appl. No.: 09/399,983

(22) Filed: Sep. 20, 1999

Related U.S. Application Data

(60) Provisional application No. 60/101,936, filed on Sep. 25, 1998.

(51) Int. Cl.[7] ...................................................... H05G 1/56
(52) U.S. Cl. ........................................... 378/114; 378/117
(58) Field of Search ............................. 378/114, 98, 117, 378/207, 118, 162, 197, 198

(56) References Cited

U.S. PATENT DOCUMENTS

| | | | |
|---|---|---|---|
| 4,392,236 | * 7/1983 | Sandstrom et al. | 378/45 |
| 4,773,086 | * 9/1988 | Fujita et al. | 378/4 |
| 5,077,771 | * 12/1991 | Skillicorn et al. | 378/102 |
| 5,081,663 | * 1/1992 | Gerlach et al. | 378/207 |
| 5,627,873 | * 5/1997 | Hanover et al. | 378/197 |

* cited by examiner

*Primary Examiner*—David P. Porta
(74) *Attorney, Agent, or Firm*—Cooper & Dunham LLP

(57) ABSTRACT

In an x-ray fluoroscopic imaging system including a portable cabinet, at least one monitor, a support arm, an articulated arm assembly connecting the support arm to the cabinet, a C-arm carried by the support arm assembly, an x-ray source and detector located at opposing locations on the C-arm, and a control panel mounted on the source or the detector, three "x-ray on" lighted indicators are disposed at visible locations in the system, one of these indicators being a switch with a light-up perimeter on the control panel, the second being incorporated in the monitor, and the third being incorporated in the cabinet.

6 Claims, 12 Drawing Sheets

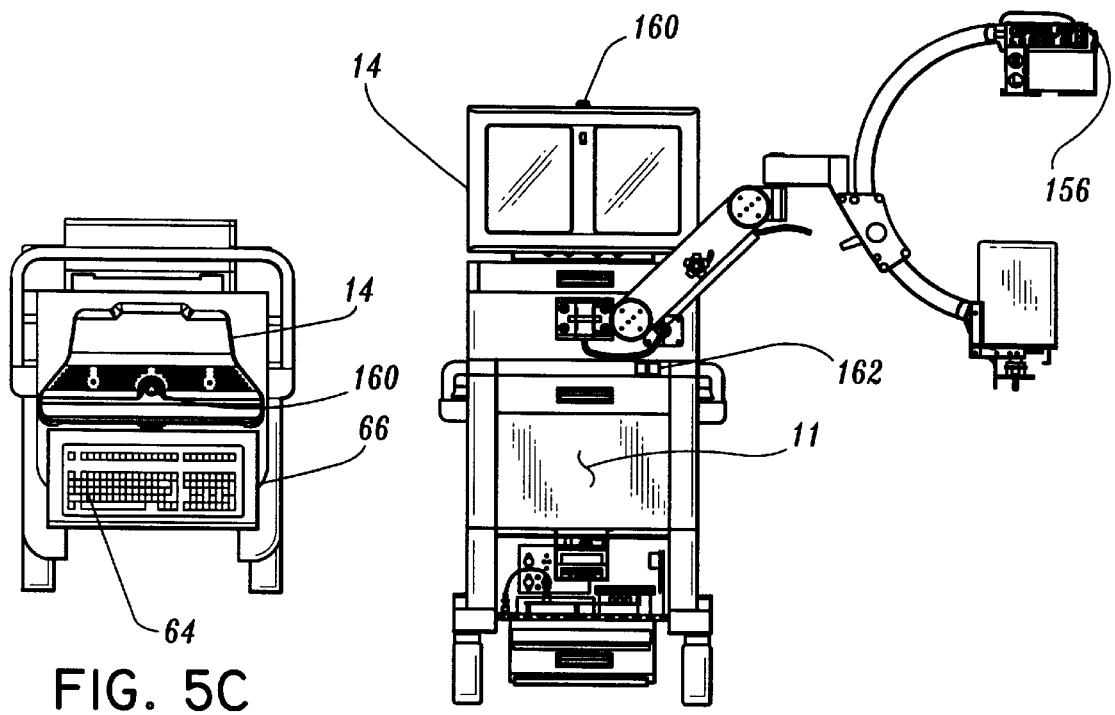
FIG. 5C
FIG. 5B
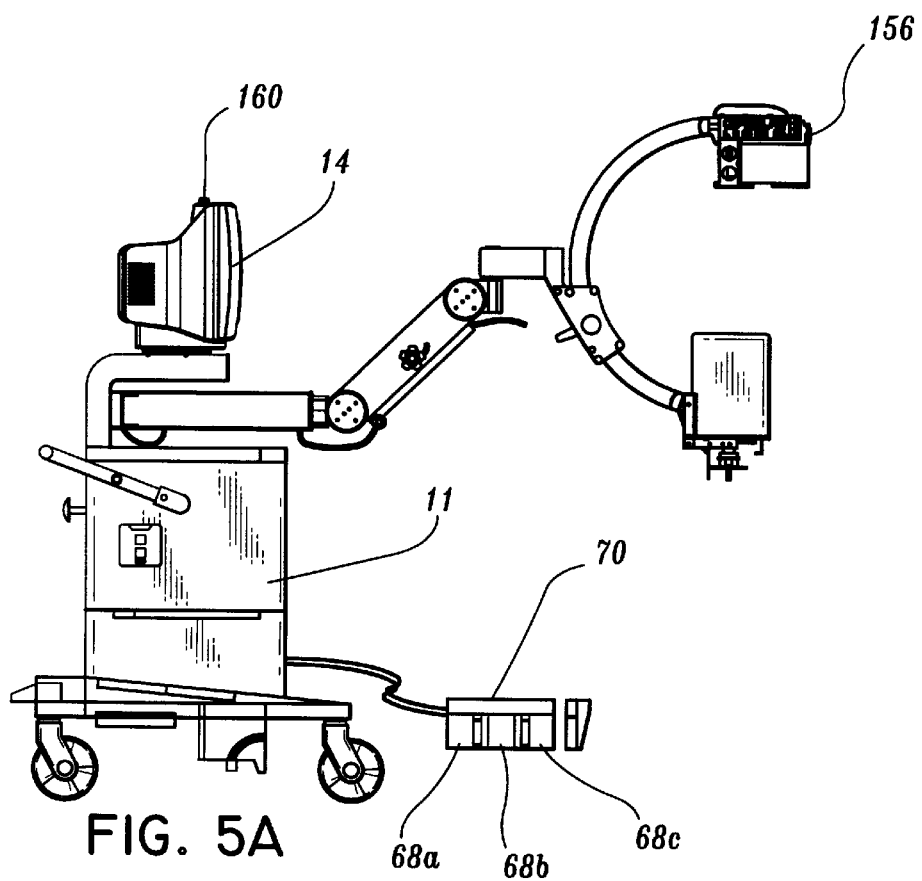
FIG. 5A

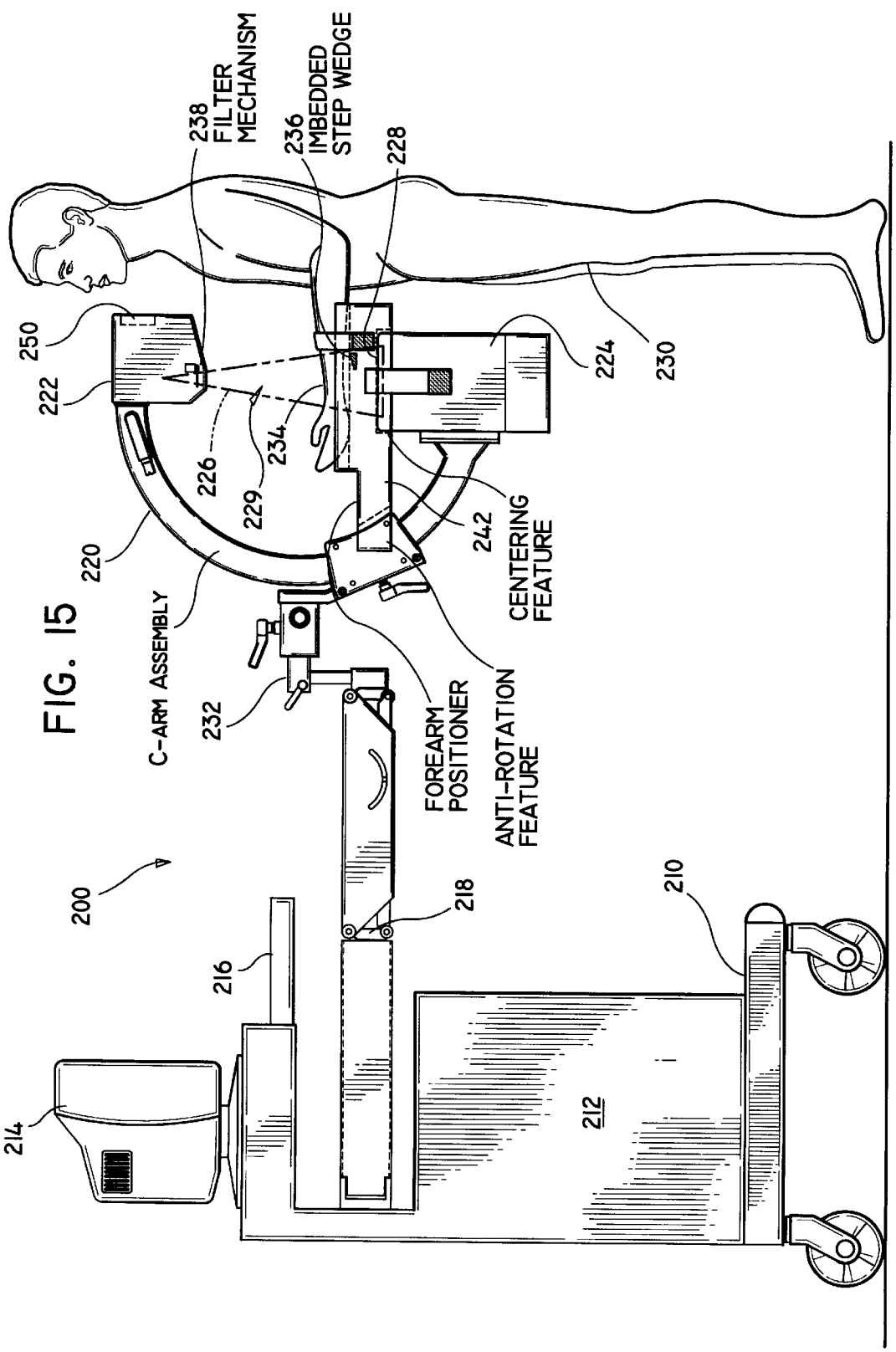

MINIATURE C-ARM APPARATUS WITH MULTIPLE X-RAY INDICATORS

CROSS REFERENCE TO RELATED APPLICATION

This application claims the priority benefit, under 35 U.S.C. §119(e)(1), of applicants' copending U.S. provisional application Ser. No. 60/101,936, filed Sep. 25, 1998, which is incorporated herein in its entirety by this reference.

BACKGROUND OF THE INVENTION

This invention relates to mobile x-ray fluoroscopic imaging systems with miniature C-arm apparatus, and more particularly to miniature C-arm apparatus providing visual indicators to alert the physician and others to the activation of the x-ray source function of the system.

In present-day medical practice, x-ray fluoroscopic imaging systems provide images of bone and tissue that are similar to conventional film x-ray shadowgrams but are produced by conversion of an incident x-ray pattern to a "live" enhanced (intensified) optical image that can be displayed on a video monitor directly, i.e., essentially contemporaneously with the irradiation of the patient's body or body portion being imaged. The term "fluoroscopic imaging" is used herein to designate such provision of directly video-displayed x-ray images. An imaging device, including an image intensifier, suitable for use in such a system is described in U.S. Pat. No. 4,142,101, which is incorporated herein in its entirety by this reference.

In some x-ray fluoroscopic imaging systems, the entire system is carried on an easily movable cart and an x-ray source and detector are mounted on a rotatable mini C-arm dimensioned for examining smaller body parts such as the extremities (wrists, ankles, etc.) of a human patient.

One illustrative example of a commercially available mini C-arm x-ray fluoroscopic imaging system is that sold under the trade name "FluoroScan III" by FluoroScan Imaging Systems, Inc., of Northbrook, Ill. Further examples of mini C-arm x-ray fluoroscopic imaging systems are described in U.S. Pat. No. 5,627,873 and copending U.S. patent application Ser. No. 09/199,952, filed Nov. 24, 1998 (and assigned to the same assignee as the present application), both of which are incorporated herein in their entirety by this reference.

Mini C-arm x-ray fluoroscopic imaging systems are also being used to measure bone mineral density (BMD) of bones in, for example, the forearm or wrist, or in the ankle or heel (calcaneal region) of a human patient. An example of such an x-ray fluoroscopic imaging system is described in allowed copending U.S. patent application Ser. No. 08/794,615 filed on Feb. 3, 1997 which is assigned to Hologic, Inc., the parent company of the assignee of the present application, and which is incorporated herein in its entirety by this reference.

Generally, such mini C-arm x-ray fluoroscopic imaging systems and x-ray bone densitometry systems are economical in space, conveniently movable (as within a hospital, clinic or physician's office) to a desired temporary location of use, and offer superior safety (owing to low levels of electric current utilization and reduced exposure of personnel to scatter radiation) as well as ease of positioning the x-ray source and detector relative to a patient's extremity for imaging. The various functions and operations of the system are conventionally controlled by buttons or switches on a control panel that is positionally associated with the cart.

X-ray fluoroscopic imaging systems of the type with which the present invention is concerned typically include a processing system, such as a computer, and peripheral devices enclosed within a portable cabinet and a C-arm apparatus that is mounted to the cabinet. The processing system controls the operation of the various components of the imaging system, provides a camera or image processing to transform in real time image data received from an image receptor for display, printing or storage, and communicates with peripheral devices. The computer may also be configured to communicate with a local area network to transfer, for example, image data to locations remote from the sterile environment. An example of a suitable processing system is a personal computer running the Windows 95®, DOS, UNIX, MacOS or other operating systems. Examples of peripheral devices include display monitors, image (or video) printers and image storage devices (or recorders).

The C-arm apparatus includes a C-arm assembly, a support arm assembly and an articulated arm assembly. The C-arm assembly includes a C-arm having a track for guiding rotational movement of the C-arm, an x-ray source assembly including an x-ray source and an x-ray detector assembly including an image receptor and camera. The x-ray source and detector assemblies are located at opposing ends of the C-arm so that the x-ray source and image receptor face each other and x-rays emitted by the x-ray source impinge on the image receptor.

The support arm assembly engages the C-arm track so that the C-arm is movable relative to the support arm, and the articulated arm assembly is provided to facilitate movement of, including change in the angular orientation of, the source and detector assemblies relative to a patient's body portion being imaged. The articulated arm assembly includes at least one movable arm wherein a first end portion of the arm is connected to the support arm assembly and a second end portion of the arm is connected to a mobile base or portable cabinet. Preferably, the first end portion is so connected to the support arm assembly that the support arm assembly can be rotated relative to the movable arm.

During surgical procedures a sterile field is created around a patient to ensure that foreign substances or organisms do not infect the patient. Any instruments or persons within this field have to be sterile or covered by a sterile draping material. The sterile field is generally defined by the American College of Surgeons and published by the Association of Operating Room Nurses (AORN). Generally, the sterile field is defined as the area occupied by the sterile draping material on any operating room table, including the patient table and instrument tables. To permit sterile personnel to position the x-ray fluoroscopic imaging system C-arm assembly in the sterile field a clear surgical drape covers the C-arm assembly.

In the x-ray fluoroscopic imaging system described in U.S. provisional patent application Ser. No. 60/078,491 filed by one of the applicants herein (jointly with other persons) on Mar. 18, 1998, and in U.S. patent application Ser. No. 09/270,373 filed by the same one of the applicants herein (jointly with the same other persons) on Mar. 16, 1999, the entire disclosures of which are both incorporated herein by this reference, to permit surgeons to activate certain functions of the x-ray fluoroscopic imaging system within this sterile field, either the x-ray source assembly or the x-ray detector assembly, which are used within the sterile field, includes a control panel that provides a physician with easy access to predefined imaging control functions associated with the x-ray fluoroscopic imaging system within the sterile field. By locating the control panel on the ends of the C-arm, a surgeon can activate the functions without placing a hand or arm in the path of the x-ray beam. Preferably, the control panel includes an array of membrane switches, wherein each switch in the array is provided to activate a function performed by the x-ray fluoroscopic imaging system. Examples of functions controlled by the control panel switches include: x-ray source activation; image printing; image noise suppression; camera rotation; and x-ray source voltage/current control.

The x-ray fluoroscopic imaging system may also include a foot control panel which is similar to the above-described control panel but permits foot activation of predefined functions of the x-ray fluoroscopic imaging system including but not limited to x-ray activation, image printing and image storing.

SUMMARY OF THE INVENTION

The present invention broadly contemplates the provision of an x-ray fluoroscopic imaging system comprising a portable cabinet; a support arm assembly; an articulated arm assembly having at least one movable arm and connecting the support arm assembly to the cabinet; and a C-arm assembly having a C-arm carried by the support arm assembly, an x-ray source assembly including an x-ray source and an x-ray detector assembly including an image receptor located at opposing locations on the C-arm such that the x-ray source and image receptor face each other so that x-rays emitted by the x-ray source impinge on the image receptor, wherein at least one of the source and image receptor assemblies includes a control panel coupled to a computer in the x-ray fluoroscopic imaging system that permits activation of predefined functions of the x-ray fluoroscopic imaging system; wherein the improvement comprises the provision of at least one "x-ray on" lighted indicator disposed at a visible location in the system.

In embodiments of the invention in which the control panel comprises an array of membrane switches, the "x-ray on" lighted indicator may be one of these switches, which is arranged to be illuminated around its entire perimeter during actual x-ray on activation. Alternatively or additionally, the "x-ray on" indicator may be an indicator incorporated in the cabinet and arranged to be illuminated when x-rays are active; and/or, in embodiments in which the system includes a monitor, the "x-ray on" indicator may be an indicator incorporated in the monitor and arranged to be illuminated when x-rays are active.

Very advantageously, and as a particular feature of the invention, the system includes at least two, and preferably all three, of the aforementioned indicators. In this way, personnel both within and outside the sterile field, and in diverse positions relative to the system, will be made aware of the x-ray on operating condition by the indicators. Moreover, the two or three indicators provide double or triple redundancy visual indicators to alert the physician and others to the activation of the x-ray source function of the system.

Further features and advantages of the invention will be apparent from the detailed description hereinbelow set forth, together with the accompanying drawings.

BRIEF DESCRIPTION OF THE DRAWINGS

FIGS. 5A, 5B and 5C are views respectively in side elevation, front elevation and plan of the apparatus of FIG. 1, showing the locations of the plural (three) "x-ray on" lighted indicators of the illustrated embodiment of the invention;

FIG. 15 is a simplified and partly schematic side elevational view of a mini C-arm x-ray fluoroscopic imaging system arranged for use to measure forearm BMD of a human patient, in which an embodiment of the present invention may be incorporated.

DETAILED DESCRIPTION

Figure 1:
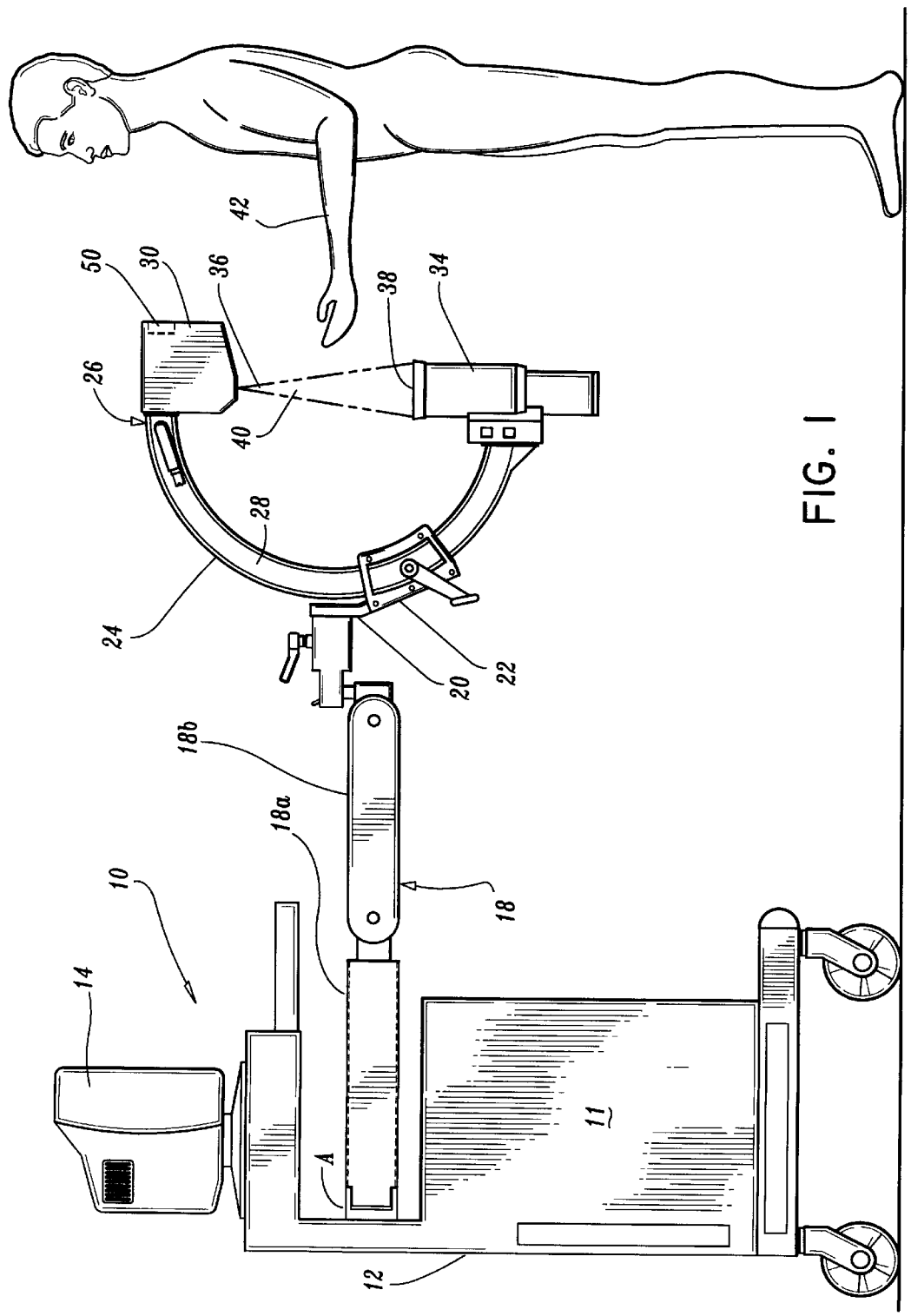
FIG. 1 is a simplified and partly schematic side elevational view of mini C-arm x-ray fluoroscopic imaging apparatus incorporating an illustrative embodiment of the present invention.
Figure 2:
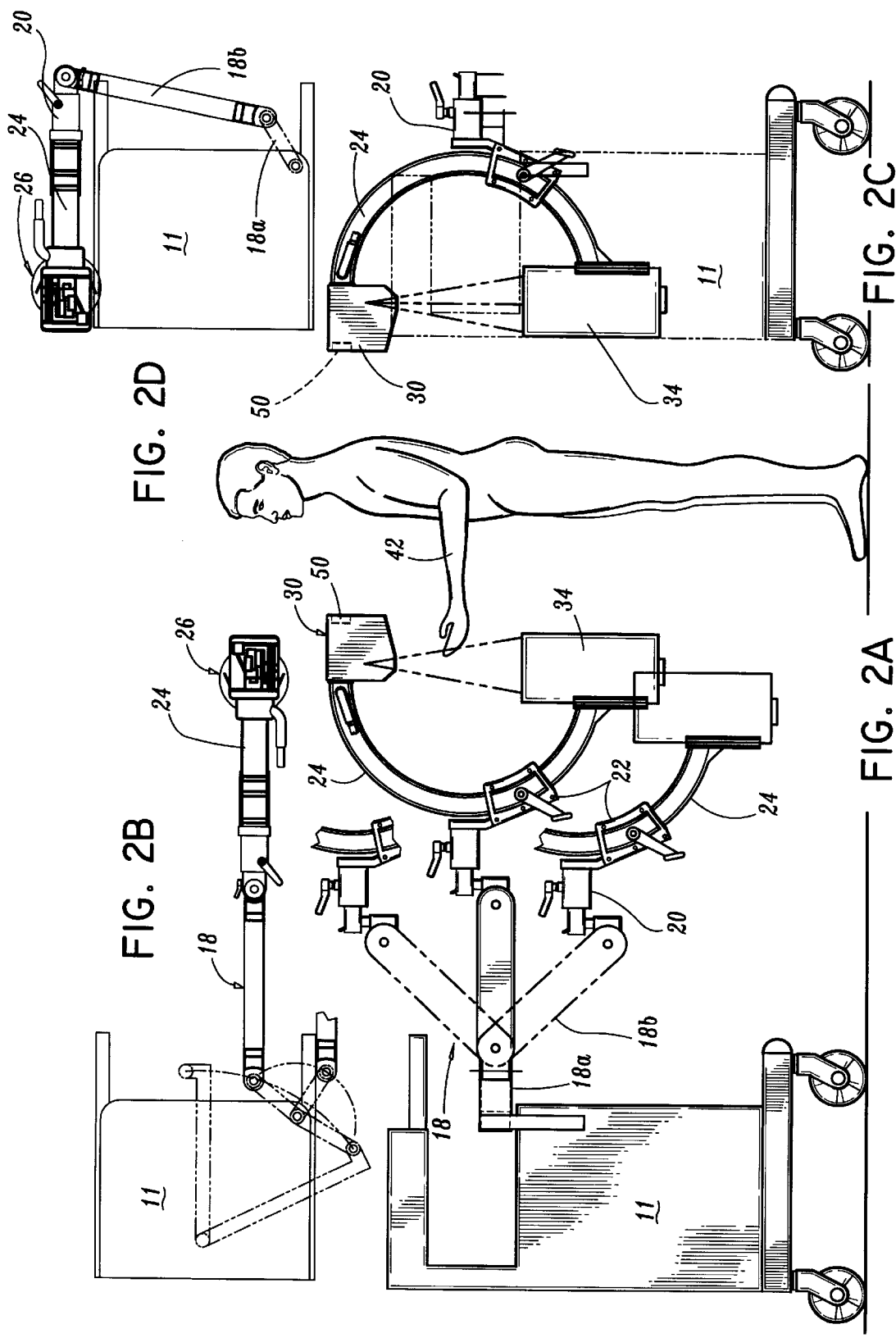
FIGS. 2A, 2B, 2C and 2D are reduced-scale views of the apparatus of FIG. 1, respectively in side elevation with the arm assembly extended (showing different positions thereof), in plan with the arm assembly extended, in side elevation with the arm assembly folded, and in plan with the arm assembly folded.
Figure 3:
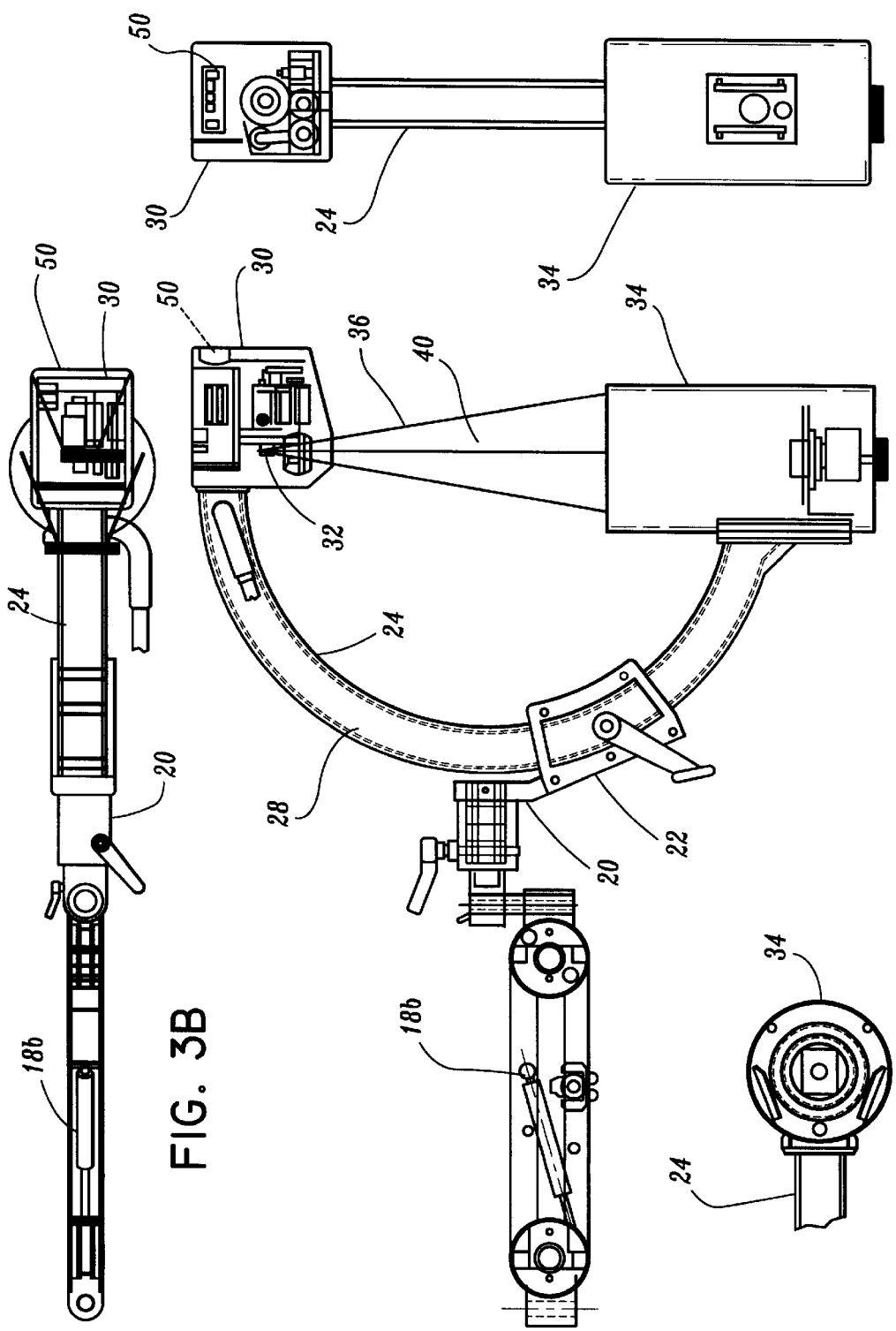
FIGS. 3A, 3B, 3C and 3D are enlarged views of a portion of FIG. 1, respectively in side elevation, top plan, fragmentary bottom plan and front elevation.

An exemplary x-ray fluoroscopic imaging system incorporating one embodiment of the present application is shown in FIGS. 1–5. In this embodiment, the imaging system 10 is entirely contained in a wheeled cart or portable cabinet 11 that can easily be rolled from place to place. The cabinet includes a generally rectangular, upright body 12 that supports a display 14 (e.g., dual video monitors) on its top surface and an articulated arm assembly 18 secured thereto. The cabinet also contains a computer for processing data as hereinafter further discussed. It will be understood that images taken by the imaging system can be shown on only a single monitor, or printed on a printer which is preferably enclosed within the cabinet.

In this embodiment, the articulating arm assembly 18 includes two arms 18a and 18b. The distal end of arm 18b is connected to a support arm assembly 20 that has a C-arm locking mechanism 22. A C-arm 24 of mini C-arm assembly 26 is carried by the support arm assembly 20 such that a track 28 of the C-arm is slid able within the C-arm locking mechanism 22. The mini C-arm assembly 26 also includes an x-ray source assembly 30 and an x-ray detector assembly 34 respectively mounted at opposite extremities of the C-arm in facing relation to each other so that an x-ray beam 36 from an x-ray source 32 within the source assembly impinges on the input end 38 of the detector assembly 34. The x-ray source 32 and detector end 38 are spaced apart by the C-arm sufficiently to define a gap 40 between them, in which the limb or extremity of a human patient 42 can be inserted in the path of the x-ray beam 36.

The support arm assembly 20 connected to the end of arm 18b provides 3-way pivotal mounting that enables the C-arm 24 to be swivelled or rotated through 360° in each of three mutually perpendicular (x, y, z) planes and to be held stably at any desired position, while the arm 18a of the articulating arm assembly 18 is mounted to the portable cabinet 11 at point "A" and jointed to enable its distal end and the C-arm to be angularly displaced both horizontally and vertically. The multidirectional angular movability of the C-arm assembly facilitates the positioning of the x-ray source and detector assemblies in relation to a patient body portion to be irradiated.

A suitable power supply for the x-ray source, and instrumentalities for controlling or varying current (mA) and voltage (kV), not shown, are incorporated in the system as well.

As noted, the C-arm 24 is movable within the C-arm locking mechanism 22. To fix the position of the C-arm relative to the support arm assembly 20, the C-arm locking mechanism is used. The C-arm locking mechanism may be a clamp assembly (not shown) which is compressed against the C-arm when tightened, but preferably the C-arm locking mechanism is of the type described in pending U.S. Provisional Patent Application No. 60/066,966 filed on Nov. 28, 1997, which is incorporated herein in its entirety by this reference.

Figure 11:
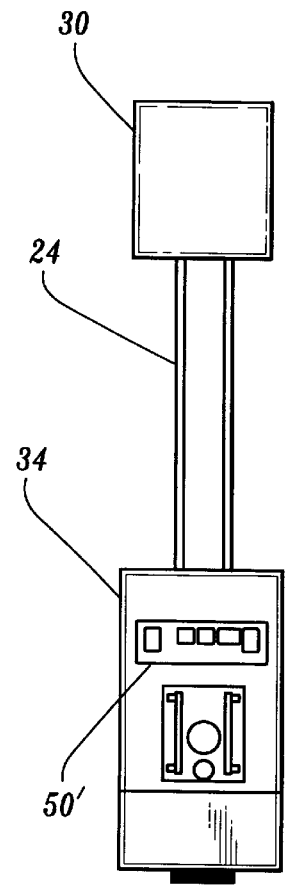
FIG. 11 is a view, similar to FIG. 3D, of a modified embodiment of the apparatus of the invention in which the C-arm control panel is mounted on the ray detector (receptor) assembly.
Figure 8:
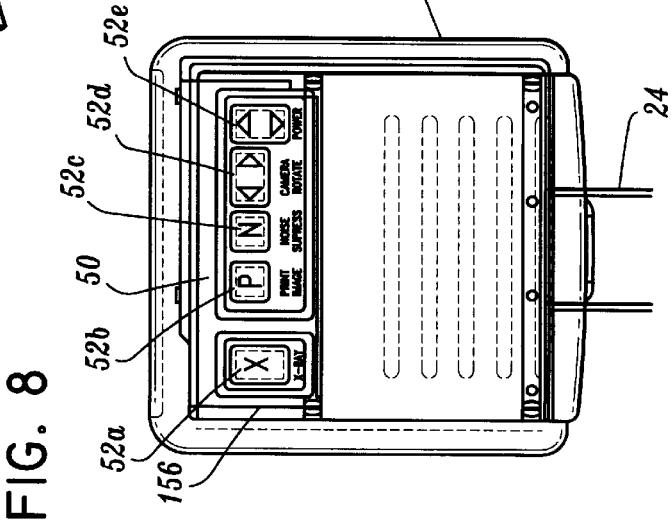

In the illustrated apparatus, either the x-ray source assembly or the x-ray detector assembly includes a control panel 50 or 50' that is mounted thereon (i.e. at one or the other of the opposed extremities of the C-arm) and is coupled to the imaging system computer to provide a physician with easy access within the sterile field to predefined imaging control functions associated with the x-ray fluoroscopic imaging system. In FIGS. 1–9, the control panel 50 is shown as mounted on the x-ray source assembly 22 at one end of the mini C-arm; in FIG. 11, the control panel 50' is illustrated as mounted on the x-ray detector assembly 34. With the control panel 50 or 50' included in either the source or detector assembly, a physician can activate certain (or all) functions of the x-ray fluoroscopic imaging system from within the sterile field and without placing a hand or arm within the path of the x-ray beam. One result of this configuration is that it gives a physician immediate control of the operating characteristics of the fluoroscope in the event that a regular operator is unavailable or unable to operate controls located outside of the sterile field. Preferably, as seen in FIG. 8, the control panel 50 includes an array of membrane switches 52a, 52b, 52c, 52d and 52e. Each switch in the array is provided to activate at least one function performed by the x-ray fluoroscopic imaging system. In one embodiment, each switch completes a signal circuit when contact material mounted on the underside of a raised button profile which provides tactile feedback is depressed to a base layer, and breaks the signal circuit when pressure on the contact material is released. As seen in FIG. 6D, each switch has a raised profile that is configured to provide a tactile response when depressed or released. This tactile response allows a physician wearing surgical gloves to feel when the switch is depressed or released.

Figure 6A:
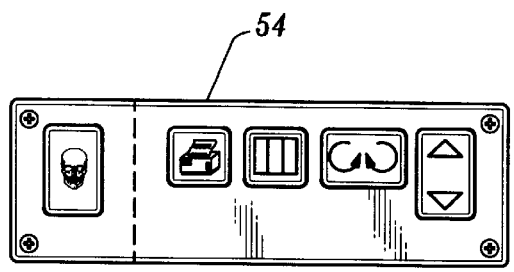
FIGS. 6A, 6B, 6C, 6D and 6E are, respectively, front elevational views of the button array, overlay, and assembled arrangement of the C-arm control panel of the apparatus of FIG. 1, and plan and side elevational views of the assembled arrangement of the control panel, including an x-ray button illuminated around the entire perimeter of the switch to serve as an "x-ray on" lighted indicator in accordance with the present invention.
Figure 6B:
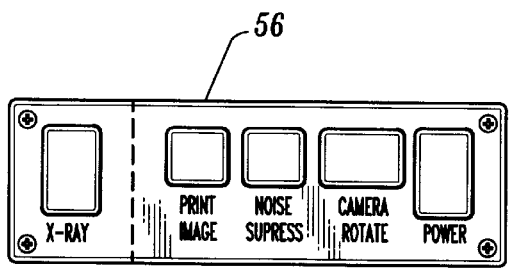
Figures 6C, 6E:
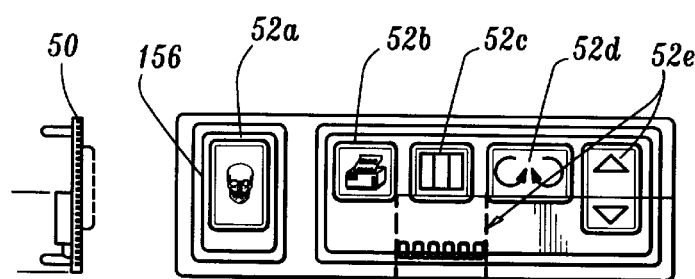
Figure 6D:
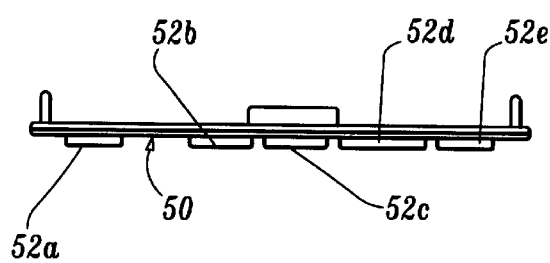
Figure 7:
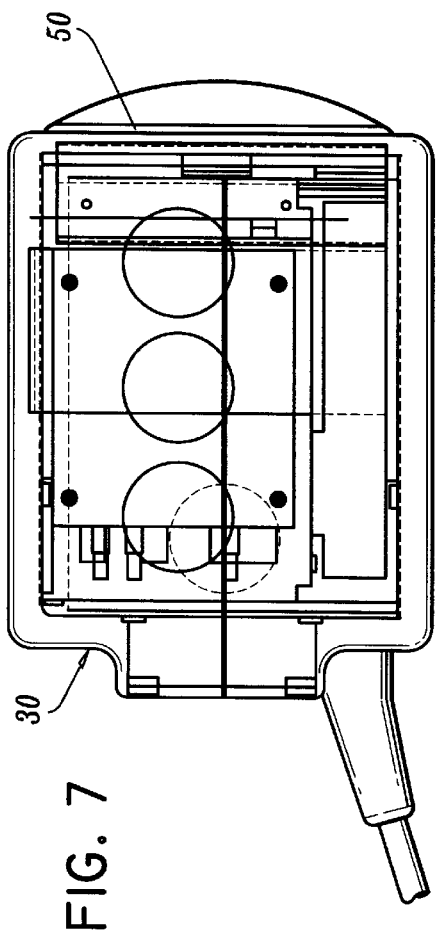
FIGS. 7, 8, and 9 are respectively top, front and side elevational views of the x-ray source assembly including the C-arm control panel in the apparatus of FIG. 1.
Figure 9:
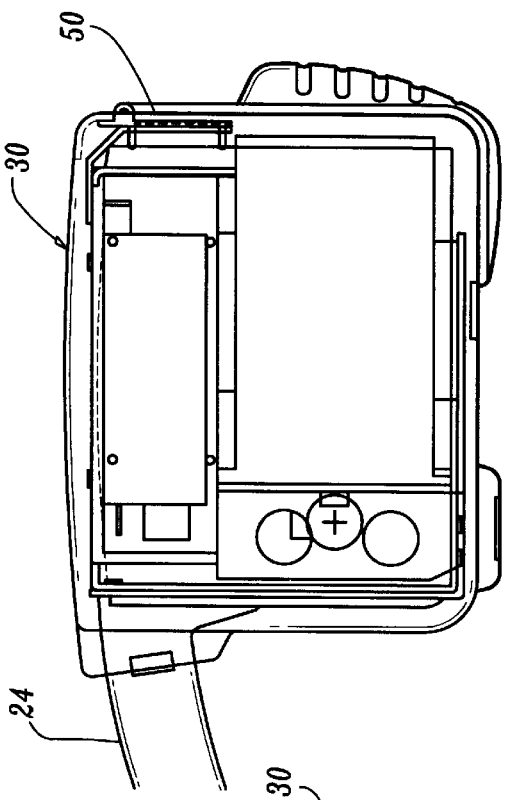

As further shown in FIGS. 6A and 6B, the control panel 50 includes a panel 54 bearing the array of membrane switches 52a–52e, and an overlay 56 with legends identifying the switches.

Examples of the functions activated by the control panel include:

X-ray Activation—One switch (designated 52a) in the array may control the x-ray source to generate a single image or for continuous imaging. For example, to generate a single image, a physician may depress the x-ray control switch twice in rapid succession and then release the switch so that the x-ray source (or tube) is activated for a single image or strobe shot. For continuous imaging, a physician depresses the x-ray control switch twice in rapid succession and then continues to depress (or hold down) the switch so that the x-ray source is activated and continues to produce x-rays for as long as the switch is depressed to create a real time continuous or cinematic fluoroscopic picture.

Print—One switch (designated 52b) in the array may control the imaging system's video printer by depressing the switch a single time. When the switch is depressed and released, the video printer is sent a signal from the system computer to print the active image.

Noise Suppression—One switch (designated 52c) in the array may control the imaging system's noise suppression processing by stepping the video frame averaging so that each time the switch is depressed the video noise suppression frame averaging is changed. For example, each depression of the switch can step the frame averaging from 0 frames to 2, 4, 8 and 16 frames successively, starting with a current frame averaging value and incrementing from there. When the frame averaging is at 16 and the switch is depressed the frame averaging value would then roll over to 0 and begin the rotation again.

Camera Rotation—One switch (designated 52d) in the array may control the imaging system's servo controlled camera mount. Activation of this switch activates a servo controller that rotates a camera mount in either a clockwise or counterclockwise direction. Feedback of the position of the camera mount within a range of travel of the servo controller may be provided by the use of a moving icon on the video display of the imaging system.

Voltage/Current Control—Typically the kV and mA settings of the imaging system are automatically set, but an up/down switch (designated 52e) in the array may allow a physician to manually control the fluoroscopic x-ray technique factors used to create an image by increasing or decreasing the kV and mA settings. Manual control can start with the current setting of the kV and mA values and can then be incrementally moved to the end points of the available settings with each depression of the up/down switch. The return to automatic control can be achieved by pressing both the up and down portions of the switch simultaneously.

Figure 10:
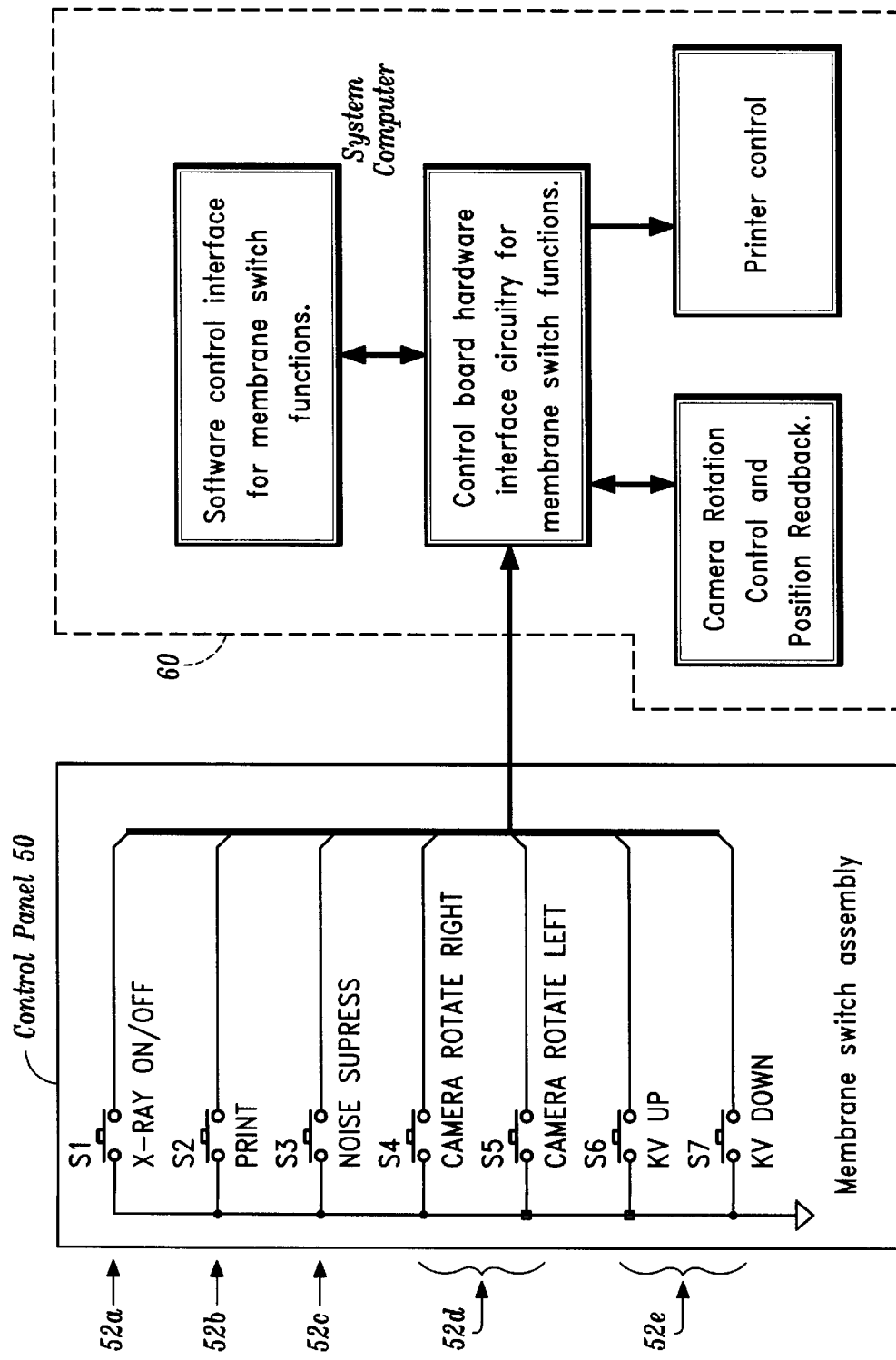
FIG. 10 is a block diagram of the control panel switches and their interaction with the system computer.

FIG. 10 provides a block diagram of the exemplary connections between the control panel switches and the system computer 60.

Figure 4:
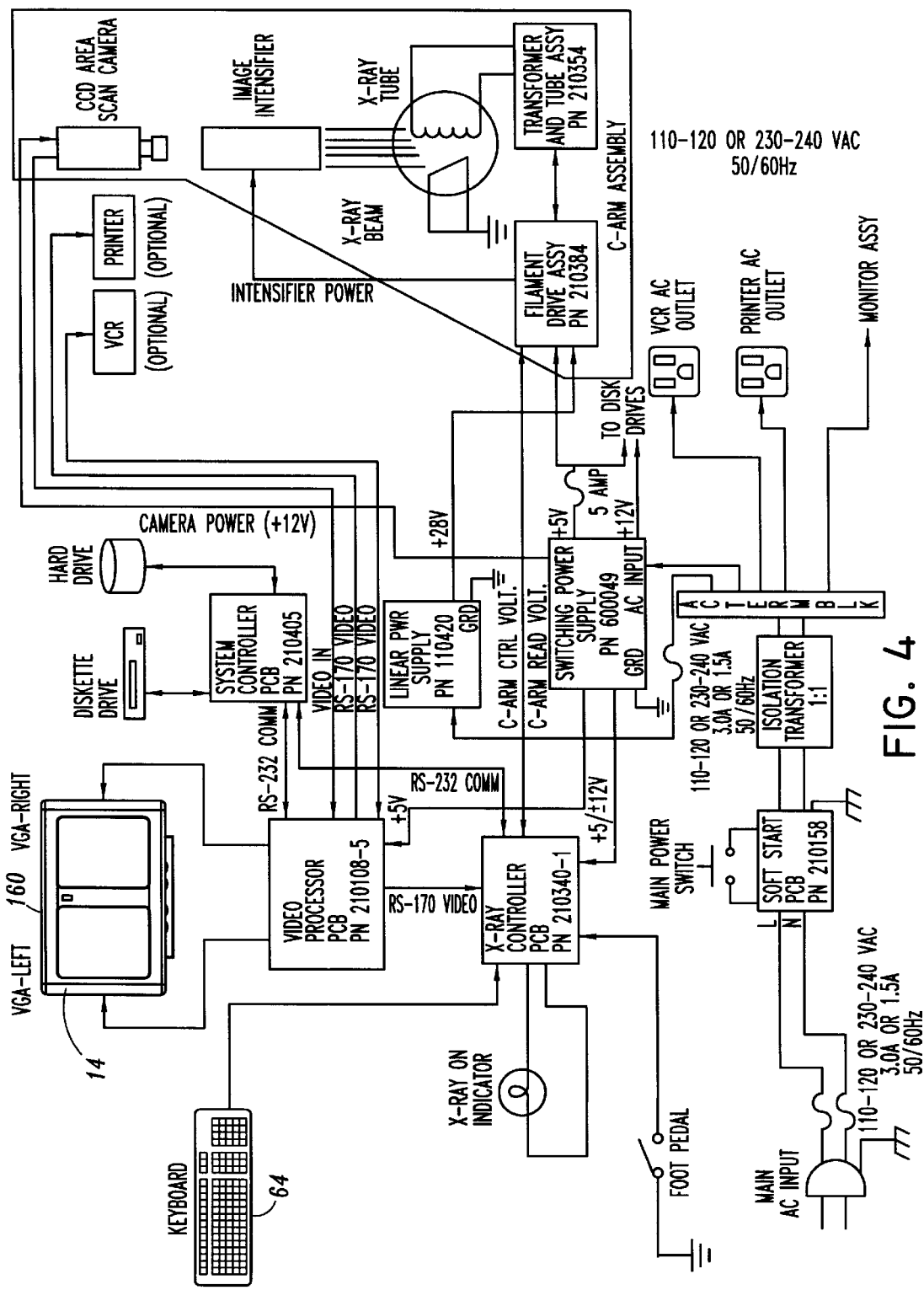
FIG. 4 is a system block diagram of the apparatus of FIG. 1.

In addition to the switches or buttons of the control panel 50 or 50' mounted on the x-ray source or detector assembly, i.e. at one end or the other of the mini C-arm, so as to be positioned within the sterile field for direct access by the physician during use of the imaging system, the apparatus of FIGS. 1–5 also includes other controls, particularly shown in FIG. 4, such as switches (not shown) on the cabinet 11, a keyboard 64 for the computer 60, supported on a sliding shelf 66 of the cabinet, and an array of foot switches 68a, 68b and 68c on a foot control panel 70 which may, if desired, also be positioned within the sterile field for operation by the physician's foot. The switches on this foot control panel permit foot activation of predefined functions of the x-ray fluoroscopic imaging system including but not limited to x-ray activation, image printing and image storing.

As thus far described, the system 10 is essentially identical to currently available mini C-arm x-ray fluoroscopic imaging systems. Thus, the system 10 may be a "FluoroScan IV" system, produced by FluoroScan Imaging Systems, Inc., having the following specifications:

OUTPUT FORMAT:
Standard 2,200 Image Storage;
Optional 4,000 Image Storage; Digital Video Output;
Composite Video Output
VIDEO PROCESSING:
Last Image Hold for 4 Images;
Real Time Edge Enhancement;
User Selectable Real Time Recursive Averaging;
Noise Suppression; Automatic Contrast Enhancement;
Automatic Brightness Control
INPUT POWER:
110V~60 Hz Nominal; 90V~to 132V~Actual; 47 Hz to 63 Hz Actual; Non Dedicated, Grounded
WARM UP: 3 Seconds
X-RAY POWER SUPPLY:
Continuous Duty kV–40 kV to 75 kV in 2.15 kV Increments
ANODE CURRENT:
20 $\mu$A (0.020 mA) to 100 $\mu$A (0.1 mA) in 3.6 $\mu$A Increments
FOCAL SPOT: 85 Micron (0.085 mm)
TUBE TYPE: Custom Designed Cold Anode
TUBE COOLING:
Maximum Tube Temperature is 50° C. at Maximum Power After 4 Hours of Continuous Duty
TARGET: Tungsten
COLLIMATION: Fixed to Field of View Size
FIELDS OF VIEW: 150 mm (6" Nominal)
IMAGE INTENSIFIER:
High Gain Micro Channel Plate with Minimum of 40,000 Gain
PIXEL ARRAY: 768 pixels by 600 lines
DUAL VIDEO MONITORS:
15" (39 cm) SVGA High Resolution Video Monitor
Video Standard NTSC/VHS
OVERALL HEIGHT: 60 inches
OVERALL FLOOR SPACE: 8.0 ft$^2$ (36" wide by 32" deep).

In accordance with the present invention, in the exemplary embodiment now to be described, there are provided three "x-ray on" lighted indicators disposed at various specific visible locations on the system, to alert physicians and other personnel to the fact that the x-ray source is activated and emitting x-rays. Each of these three indicators comprises or includes a light that becomes illuminated when the x-ray source is activated and remains illuminated for the duration of such activation, ceasing to be illuminated upon de-activation of the x-ray source.

Figure 12A:
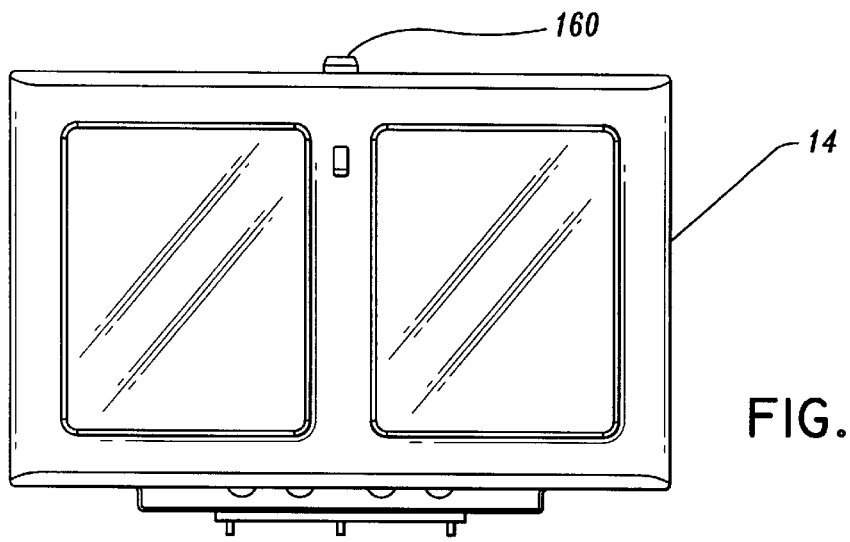
FIGS. 12A, 12B and 12C are views respectively in front elevation, side elevation and plan of the dual monitors of the apparatus of FIG. 1 incorporating an "x-ray on" lighted indicator in accordance with the invention.
Figure 12C:
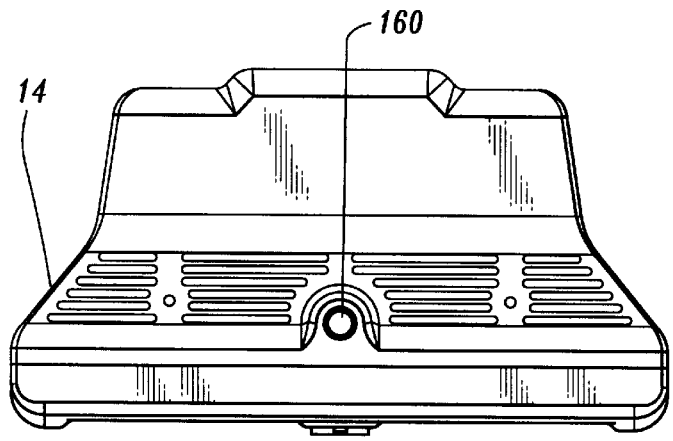
Figure 12B:
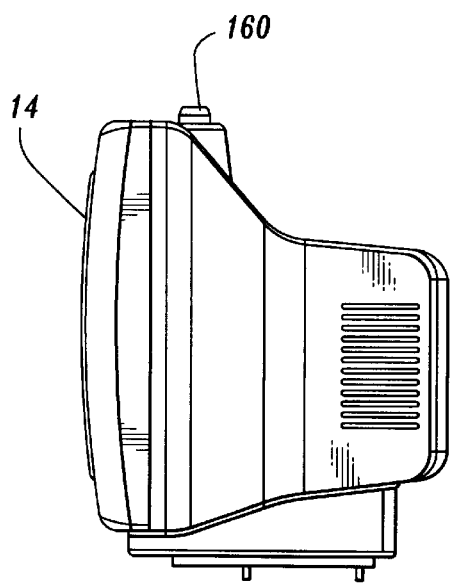
Figure 13:
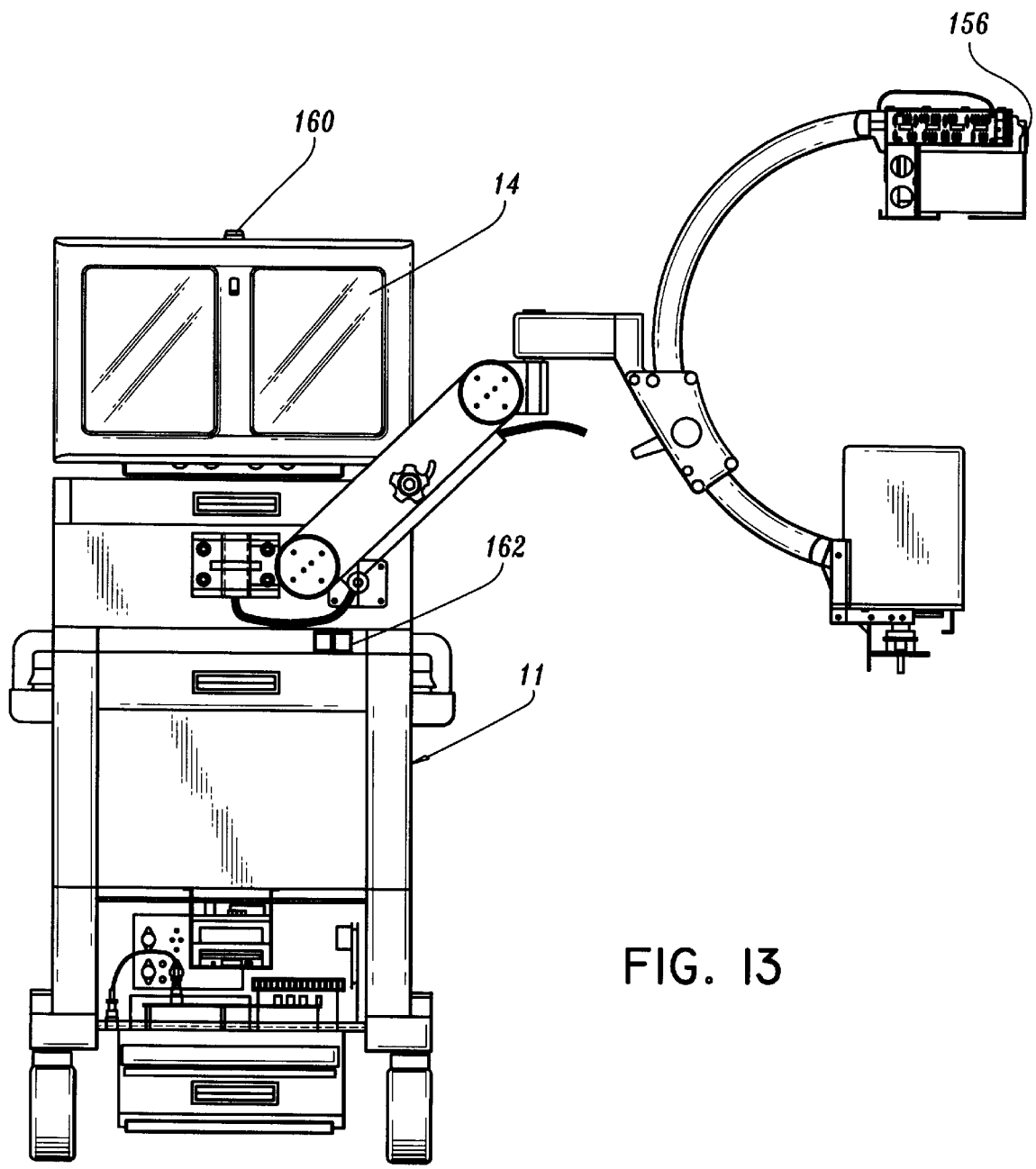
FIG. 13 is a front elevational view of the cabinet of the apparatus of FIG. 1 incorporating an "x-ray on" lighted indicator in accordance with the invention.

One of these "x-ray on" lighted indicators includes a light 156 (FIG. 14) incorporated in the x-ray switch 52a of the control panel 50 as shown in FIG. 6; the light 156 causes the x-ray switch 52a to be illuminated around its entire perimeter during actual x-ray activation. The second of the "x-ray on" lighted indicators comprises a light 160 incorporated in, i.e., mounted on top of, the dual video monitors 14 as shown in FIGS. 12A–12C. The third of the "x-ray on" indicators is a light 162 incorporated in, i.e., mounted on the front of, the portable cabinet 11 as shown in FIG. 13. The distribution of all three indicators in the complete system is shown in FIGS. 5A–5C.

Figure 14:
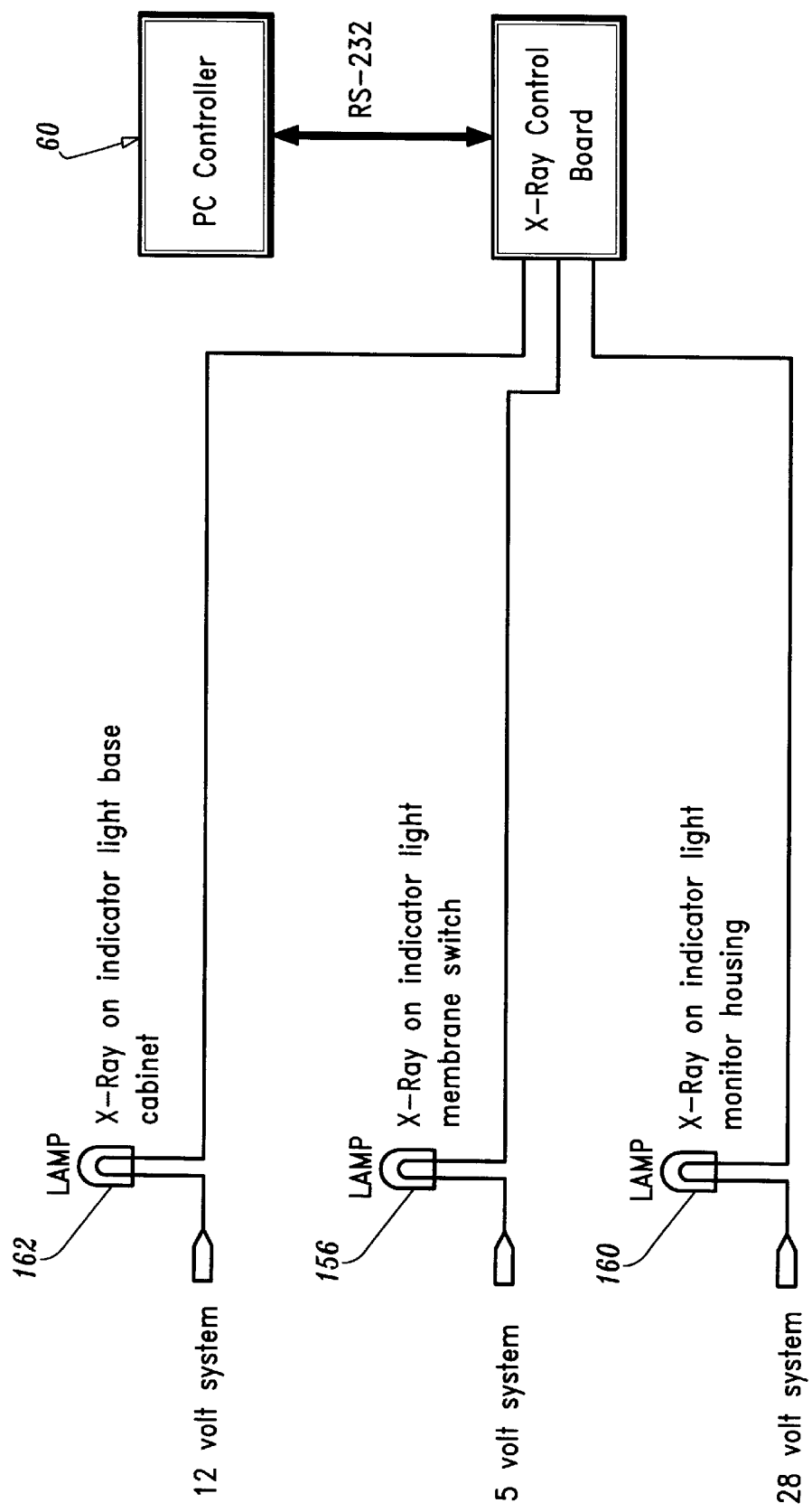
FIG. 14 is a block diagram of the "x-ray on" indicators and their interaction with the system computer.

FIG. 14 is a block diagram of exemplary connections electrical connections between the three "x-ray on" indicators 156, 160 and 162, and the system computer 60.

A wide variety of additional alternatives are embraced within the scope of the invention in its broader aspects. For instance, the image intensifier employed in the detector may be either of a type that intensifies optical images (as in the above-described "FluoroScan IV" system) or of a type that intensifies x-ray images. Again, in place of an image intensifier and video camera, the detector may be a direct digital 2-dimensional x-ray detector; an example of such a device is the "FlashScan 20" high resolution flat panel device of dpiX, A Xerox Company, which is an amorphous silicon image sensor that acquires conventional x-ray images and converts them to digital form in a way that can provide fluoroscopic imaging in real time.

An alternative embodiment of an x-ray fluoroscopic imaging system in which the present invention can be incorporated is that described in the aforementioned copending U.S. patent application Ser. No. 08/794,615, which describes various alternative embodiments and modifications suitable for such use.

Such an alternative embodiment of the x-ray fluoroscopic imaging system which can be used to measure bone mineral density (BMD) in, for example, the forearm, wrist, ankle or heel of a human patient will be described with reference to FIG. 15. This imaging system 200 is also entirely contained in a wheeled cart or cabinet 210 that can easily be rolled from place to place. The cabinet includes a generally rectangular, upright body.212 that supports dual video monitors 214 (only one being shown) on its top surface and has, in its upper portion, a keyboard 216 and an articulated member 218; the cabinet also contains a computer (not shown) for processing data as hereinafter further discussed. It will be understood that the present method can be practiced with use of only a single monitor, or indeed without a monitor (e.g., employing a printer to produce the BMD measurement data).

The outer end of articulated member 218 carries a mini C-arm 220 having an x-ray source 222 and a detector 224 respectively fixedly mounted at its opposite extremities so that an x-ray beam 226 from source 222 impinges on the input end 228 of the detector, the source and detector being spaced apart by the C-arm sufficiently to define a gap 229 between them, in which the limb or extremity of a human patient 230 can be inserted in the path of the x-ray beam 226. The C-arm is connected to the end of member 218 by a 3-way pivotal mounting 232 that enables the C-arm to be swivelled or rotated through 360° in each of three mutually perpendicular (x, y, z) planes and to be held stably at any desired position, while the member 218 is itself mounted and jointed to enable its outer end and the C-arm to be angularly displaced both horizontally and vertically. The multidirectional angular movability of the mini C-arm facilitates the positioning of the source and detector in relation to a patient body portion to be irradiated.

Preferably, either the x-ray source or the x-ray detector includes a control panel 250 that is coupled to the imaging system computer to provide a physician with easy access within the sterile field to predefined imaging control functions associated with the x-ray fluoroscopic imaging system. The control panel 250 is illustrated in FIG. 15 as being mounted on the detector 224. Preferably, the control panel 250, like the panel 50 of FIG. 8, includes an array of membrane switches, each of which is provided to activate at least one function performed by the x-ray fluoroscopic imaging system. In one embodiment, each switch in the array has a raised button profile which provides tactile feedback, completes a signal circuit when contact material mounted on the underside of the raised button profile which provides tactile feedback is depressed to a base layer and breaks the signal circuit when pressure on the contact material is released.

A suitable power supply for the x-ray source, and instrumentalities for controlling or varying current (mA) and voltage (kV), not shown, are incorporated in the system as well.

The beam 226 emitted by the x-ray source 222 is a cone-shaped beam (i.e. a volume beam as opposed to a pencil beam or fan beam) that impinges on a flat x-ray-sensitive receiving surface of the detector 224 at or adjacent the detector input end; this receiving surface faces the source across the gap 229 and is perpendicular to the axis of the beam path, so that the intersection of the receiving surface and the conical x-ray beam is an extended circular (2-dimensional) area. The term "field of view" is used herein to refer to the latter circular area, or that portion of it to which the detector responds, and also to designate the region, within the beam path or gap 229, the contents of which will be imaged by the detector. It will be understood that the area of the field of view as measured in a plane transverse to the beam path axis is sufficient to encompass objects of the size desired to be imaged or otherwise studied, e.g. a human wrist or heel.

The receiving surface of the detector 224 is a surface of an x-ray-to-visible-light converter, such as a layer of phosphor or scintillator material covered externally by a light shield, that converts impinging x-rays to visible light. The detector may include a Cesium Iodide vacuum tube image intensifier or an image intensifier of the high-gain microchannel plate type, and a planar output surface on which is produced an output visible-light image of the field of view, in accordance with well-known principles of fluoroscopic imaging. The combined converter and image intensifier elements of the detector 224 may be as described in the aforementioned U.S. Pat. No. 4,142,101 which is incorporated herein by reference.

In addition, the detector assembly includes a video camera (not separately shown) for viewing the image on the aforementioned planar output surface and producing a signal output representative of that viewed image. The video camera can be a television camera and can operate according to a video standard such as NTSC or CCIR. When the system is employed for fluoroscopic imaging, the signal output of the video camera is processed by the onboard computer to produce video images on one or both monitors 214; the system also includes devices for recording and, optionally, printing out these video fluoroscopic images.

As thus far described, the system 200 is essentially identical to currently available mini C-arm x-ray fluoroscopic imaging systems, e.g. having specifications as set forth above for the system 10 of FIG. 1.

In this system, in accordance with the present invention, a plurality of "x-ray on" lighted indicators are provided, for example in locations corresponding to those described above with reference to the apparatus 10 of FIGS. 1–14.

Since the detector in the fluoroscopic imaging system detects x-ray emission from a cone-beam source over an extended two-dimensional area (the cross-section of the x-ray beam path in the plane of the detector receiving surface), there is inherent variation (i.e., variation attributable to the source and/or the detector having the image intensifier, independent of attenuation by any object interposed in the beam path) in received radiation intensity over the field of view. The image data obtained for the wrist and calibration bone sample by the steps described above are corrected for this inherent variation in order to enable more accurate calculation of BMD.

The calculation of data to produce BMD measurements could be performed with an onboard computer in a mini C-arm fluoroscopic system such as the "FluoroScan III" system, or in another computer. The functions of data acquisition/storage and BMD computation therefrom could be performed by different computers. Also, instead of digitizing the detector output data before conversion to logarithms, the logarithmic conversion could be performed first (e.g. with a log amplifier) and digitized thereafter. Moreover, in addition to or in place of the fixtures described above for holding the body portion stationary, appropriate software could be employed to re-register the images if there is movement.

A more detailed description of this embodiment and its operation is provided in the aforementioned U.S. application Ser. No. 08/794,615 which is incorporated herein by reference.

It is to be understood that the invention is not limited to the procedures and embodiments hereinabove specifically set forth, but may be carried out in other ways without departure from its spirit.

What is claimed is:

1. An x-ray fluoroscopic imaging system comprising:
   a portable cabinet;
   a support arm assembly;
   an articulated arm assembly having at least one movable arm and connecting said support arm assembly to said portable cabinet; and
   a C-arm assembly having a C-arm carried by said support arm assembly, an x-ray source assembly including an x-ray source and an x-ray detector assembly including an image receptor located at opposing locations on the C-arm such that said x-ray source and image receptor face each other so that x-rays emitted by said x-ray source impinge on said image receptor, wherein at least one of said source and image receptor assemblies includes a control panel comprising an array of switches coupled to a computer in said x-ray fluoroscopic imaging system that permits activation of predefined functions of the x-ray fluoroscopic imaging system; and
   at least one "x-ray on" lighted indicator disposed at a visible location in the system, said one "x-ray on" lighted indicator comprising one of said switches.

2. An x-ray fluoroscopic imaging system as defined in claim 1, wherein said control panel comprises an array of membrane switches, and wherein said one of said switches is illuminated around its perimeter during actual x-ray on activation.

3. An x-ray fluoroscopic imaging system comprising:
   a portable cabinet;
   at least one monitor;
   a support arm assembly;
   an articulated arm assembly having at least one movable arm and connecting said support arm assembly to said portable cabinet; and a C-arm assembly having a C-arm carried by said support arm assembly, an x-ray source assembly including an x-ray source and an x-ray detector assembly including an image receptor located at opposing locations on the C-arm such that said x-ray source and image receptor face each other so that x-rays emitted by said x-ray source impinge on said image receptor, wherein at least one of said source and image receptor assemblies includes a control panel comprising an array of membrane switches coupled to a computer in said x-ray fluoroscopic imaging system that permits activation of predefined functions of the x-ray fluoroscopic imaging system; and at least two "x-ray on" lighted indicators each disposed at a visible location in the system, and arranged to be illuminated when x-rays are active, one of said two "x-ray on" lighted indicators comprising one of said switches.

4. The x-ray fluoroscopic imaging system according to claim 3, wherein said one of said switches is illuminated around its perimeter during actual x-ray on activation; and wherein the other of said two indicators is an indicator incorporated in the monitor and arranged to be illuminated when x-rays are active.

5. The x-ray fluoroscopic imaging system according to claim 3, wherein said one of said switches is illuminated around its perimeter during actual x-ray on activation; and wherein the other of said two indicators is an indicator incorporated in the cabinet and arranged to be illuminated when x-rays are active.

6. An x-ray fluoroscopic imaging system comprising:

a portable cabinet;

at least one monitor;

a support arm assembly;

an articulated arm assembly having at least one movable arm, and connecting said support arm assembly to said portable cabinet; and a C-arm assembly having a C-arm carried by said support arm assembly, an x-ray source assembly including an x-ray source and an x-ray detector assembly including an image receptor located at opposing locations on the C-arm such that said x-ray source and image receptor face each other so that x-rays emitted by said x-ray source impinge on said image receptor, wherein at least one of said source and image receptor assemblies includes a control panel comprising an array of membrane switches coupled to a computer in said x-ray fluoroscopic imaging system that permits activation of predefined functions of the x-ray fluoroscopic imaging system; and at least three "x-ray on" lighted indicators each disposed at a visible location in the system, said three indicators being, respectively, one of said switches, which is illuminated around its perimeter during actual x-ray on activation; an indicator incorporated in the monitor and arranged to be illuminated when x-rays are active; and an indicator incorporated in the cabinet and arranged to be illuminated when x-rays are active.

* * * * *